(12) United States Patent
Bruck et al.

(10) Patent No.: US 6,635,255 B1
(45) Date of Patent: Oct. 21, 2003

(54) CASB414:ANTIGEN OVEREXPRESSED IN SEVERAL TUMORS

(75) Inventors: Claudine Elvire Marie Bruck, Rixensart (BE); Jean-Pol Cassart, Lustin (BE); Thierry Coche, Namur (BE); Carlota Vinals Y De Bassols, Brussels (BE)

(73) Assignee: SmithKline Beecham Biologicals s.a., Rixensart (BE)

( * ) Notice: Subject to any disclaimer, the term of this patent is extended or adjusted under 35 U.S.C. 154(b) by 0 days.

(21) Appl. No.: 09/646,693

(22) PCT Filed: Mar. 17, 1999

(86) PCT No.: PCT/EP99/01893
§ 371 (c)(1),
(2), (4) Date: Dec. 18, 2000

(87) PCT Pub. No.: WO99/49033
PCT Pub. Date: Sep. 30, 1999

(30) Foreign Application Priority Data

Mar. 20, 1998 (GB) ............................................ 9806104

(51) Int. Cl.$^7$ ............................................ A61K 39/00
(52) U.S. Cl. ................. 424/185.1; 435/69.1; 435/69.3; 435/320.1; 435/325; 536/23.4; 536/23.5; 424/277.1; 530/350
(58) Field of Search ................................ 530/350, 300; 536/23.5, 23.4; 435/320.1, 325, 70.1, 69.1, 69.3; 424/185.1, 277.1

(56) References Cited

U.S. PATENT DOCUMENTS 6,146,849 A * 11/2000 Pierce et al. ................ 435/69.1

OTHER PUBLICATIONS

Database GenBank Accession No. X54529, Direct Submission, Ding, SW, Aug. 23, 1990, *Belladonna mottle* virus VP gene for virion protein and ORF.*
Database GenBank Accession No. G37079, Unpublished, Meyers, RM, 1997, SHGC–56818 human *Homo sapiens* STS genomic.*
Database GenBank Accession No. X82626, Direct Submission, Chang, BY, Nov. 7, 1994, *X. laevis* mRNA for cortical granule lectin.*
Database GenBank Accession No. AW073901, Unpublished, NCI–CGAP, 1997, xb04g03.x1 NCI CGAP Gu1 *Homo sapiens* cDNA clone, Image: 2575348 3' similar to TR: O88310 INTELECTIN; mRNA sequence.*
Database GenBank Accession No. U22347, Direct Submission, Eraso, J, Mar. 7, 1995, *Rhodobacter sphaeoides* putative photosynthesis response regulator A (prrA) gene, partial cds, and membrane–anchored protein (prrC) and putative sensor . . . .*

Gura, T. 1997, Systems for identifying drugs are ofter faulty, Science, vol. 278, pp. 1041–1042.*
Bodey, B, et al, 2000, Failure of cancer vaccines: the significant limitations of this approach to immunotherapy, Anticancer Research, vol. 20, pp. 2665–2676.*
Lee, K–H, et al, 1999, Increased vaccine–specific T cell frequency after peptide–based vaccination correlates with increased susceptibility to in vitro stimulation but does not lead to tumor regression, Journal of Immunology, vol. 163, pp. 6292–6300.*
Bergers, G, et al, 2000, Extrinsic regulators of epithelial tumor progression: metalloproteinases, Current Opinion in Genetics & Development, vol. 10, pp. 120–127.*
Ezzell, C, 1995, Cancer "vaccines": an idea whose time has come?, Journal of NIH Research, vol. 7, pp. 46–49.*
Zaks, TZ, et al, 1998, Immunization with a peptide epitope (p369–377) from HER–2/neu to peptide–specific cytotoxic T lymphocytes that fail to recognize HER–2/neu+ tumors, Cancer Research, vol. 58, pp. 4902–4908.*
Splitler, LE, 1995, Cancer vaccines: the interferon analogy, Cancer Biotherapy, vol. 10, No. 1, pp. 1–3.*
Sinkovics, JG, et al, 2000, Vaccination against human cancers (review), International Journal of Cancer, vol. 16, pp. 81–96.*
Gao, P, et al, 2000, Tumor vaccination that enhances anti–tumor T–cell responses does not inhibit th growth of established tumors, Journal of Immunotherapy, vol. 23, No. 6, pp. 643–653.*
Bowie, JU, et al, 1990, Deciphering the message in protein sequences: tolerance to amino acid substitutions, Science, vol. 247, pp. 1306–1310.*
Burgess, WH, et al, 1990, Possible dissociation of the heparin–binding and mitogenic activities of heparin–binding (acidic fibroblast) growth factor–1, J Cell Biology, vol. 111, pp. 2129–2138.*
Lazar, E, et al, 1988, Transforming growth factor alpha: mutation of aspartic acid 47 and leucine 48 results in different biological activities, Molecular and Cellular Biology, vol. 8, pp. 1247–1252.*

* cited by examiner

Primary Examiner—Anthony C. Caputa
Assistant Examiner—Stephen L. Rawlings
(74) Attorney, Agent, or Firm—Edward R. Gimmi; Teresa O. Bittenbender

(57) ABSTRACT

CASB414 polypeptides and polynucleotides and methods for producing such polypeptides by recombinant techniques are disclosed. Also disclosed are methods for utilizing CASB414 polypeptides and polynucleotides in diagnostics, and vaccines for prophylactic and therapeutic treatment of cancers, particularly colon cancers, autoimmune diseases, and related conditions.

4 Claims, 4 Drawing Sheets

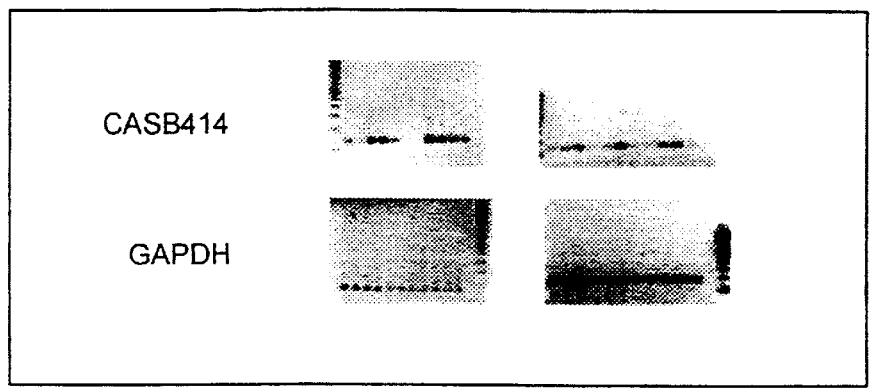

Figure 1:
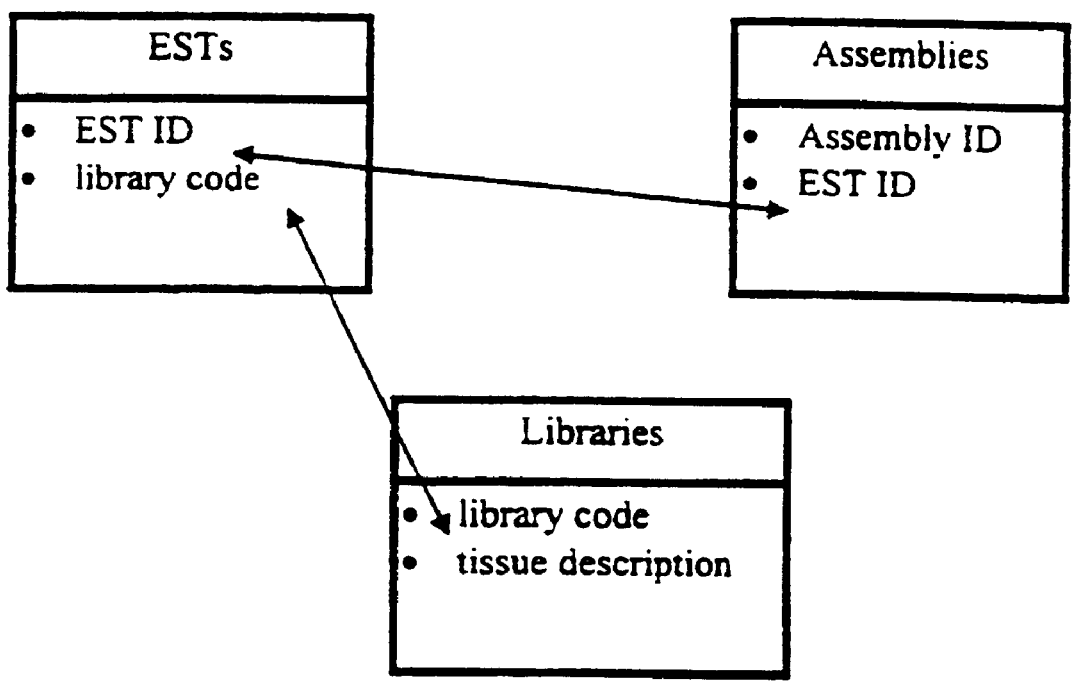

Fig.3 Detection of CASB414 mRNA in 19 normal tissues and 3 tumour samples by RT-PCR.

Lanes from left to right are (normal tissue: N; tumour tissue: T): NTC, breast(N), breast (T), colon (N), colon (T), lung (N), lung (T), brain (N), heart (N), kidney (N), oesophagus (N), bladder (N), cervix (N), muscle (N), pancreas (N), placenta (N), rectum (N), skin (N), spleen (N), stomach (N), testis (N), uterus (N), NTC. Transcripts are detected at significant levels in normal and tumour colon, normal heart, kidney, liver, oesophagus, muscle, stomach and testis.

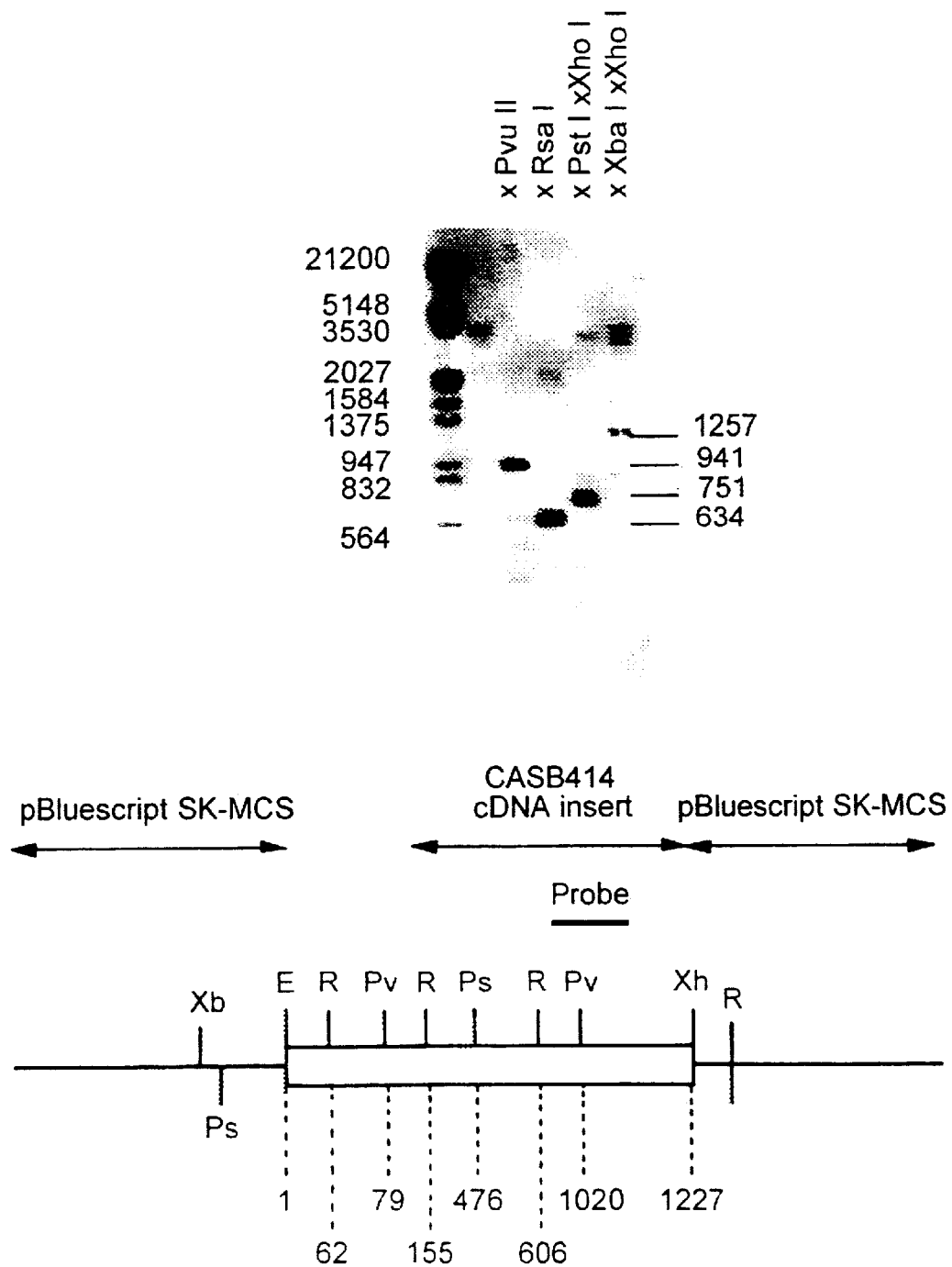
Fig.4 Southern blot analysis of CASB414 on restricted cDNA library

CASB414:ANTIGEN OVEREXPRESSED IN SEVERAL TUMORS

The present invention relates to polynucleotides, herein referred to as CASB414 polynucleotides, polypeptides encoded thereby (referred to herein as CASB414 polypeptides), recombinant materials and methods for their production. In another aspect. the invention relates to methods for using such polypeptides and polynucleotides, including the treatment of cancer and autoimmune diseases and other related conditions. In a further aspect, the invention relates to methods for identifying agonists and antagonists/inhibitors using the materials provided by the invention, and treating conditions associated with CASB414 polypeptide imbalance with the identified compounds. In a still further aspect, the invention relates to diagnostic assays for detecting diseases associated with inappropriate CASB414 polypeptide activity or levels.

Polypeptides and polynucleotides of the present invention are believed to be important immunogens for specific prophylactic or therapeutic immunization against tumours, because they are specifically expressed or highly overexpressed in tumours compared to normal cells and can thus be targeted by antigen-specific immune mechanisms leading to the destruction of the tumour cell. They can also be used to diagnose the occurrence of tumour cells. Furthermore, their inappropriate expression in certain circumstances can cause an induction of autoimmune, inappropriate immune responses, which could be corrected through appropriate vaccination using the same polypeptides or polynucleotides. In this respect the most important biological activities to our purpose are the antigenic and immunogenic activities of the polypeptide of the present invention. A polypeptide of the present invention may also exhibit at least one other biological activity of a CASB414 polypeptide, which could qualify it as a target for therapeutic or prophylactic intervention different from that linked to the immune response.

Functional genomics relies heavily on high-throughput DNA sequencing technologies and the various tools of bioinformatics to identify gene sequences of potential interest from the many molecular biology databases now available, cDNA libraries enriched for genes of relevance to a particular tissue or physiological situation can be constructed using recently developed subtractive cloning strategies. Furthermore, cDNAs found in libraries of certain tissues and not others can be identified using appropriate electronic screening methods.

High throughput genome- or gene-based biology allows new approaches to the identification and cloning of target genes for useful immune responses for the prevention and vaccine therapy, of diseases such as cancer and autoimmunity.

In a first aspect, the present invention relates to CASB414 polypeptides. Such peptides include isolated polypeptides comprising an amino acid sequence which has at least 70% identity, preferably at least 80% identity, more preferably at least 90% identity, yet more preferably at least 95% identity, most preferably at least 97–99% identity, to that of SEQ ID NO:2 over the entire length of SEQ ID NO:2. Such polypeptides include those comprising the amino acid of SEQ ID NO:2.

Further peptides of the present invention include isolated polypeptides in which the amino acid sequence has at least 70% identity, preferably at least 80% identity, more preferably at least 90% identity, yet more preferably at least 95% identity, most preferably at least 97–99% identity, to the amino acid sequence of SEQ ID NO:2 over the entire length of SEQ ID NO:2. Such polypeptides include the polypeptide of SEQ ID NO:2.

Further peptides of the present invention include isolated polypeptides encoded by a polynucleotide comprising the sequence contained in SEQ ID NO:1.

The invention also provides an immunogenic fragment of a CASB414 polypeptide, that is a contiguous portion of the CASB414 polypeptide which has the same or similar immunogenic properties to the polypeptide comprising the amino acid sequence of SEQ ID NO:2. That is to say, the fragment (if necessary when coupled to a carrier) is capable of raising an immune response which recognises the CASB414 polypeptide. Such an immunogenic fragment may include, for example, the CASB414 polypeptide lacking an N-terminal leader sequence, a transmembrane domain or a C-terminal anchor domain. In a preferred aspect the immunogenic fragment of CASB414 according to the invention comprises substantially all of the extracellular domain of a polypeptide which has at least 70% identity, preferably at least 80% identity, more preferably at least 90% identity, yet more preferably at least 95% identity. most preferably at least 97–99% identity, to that of SEQ ID NO:2 over the entire length of SEQ ID NO:2

The polypeptides or immunogenic fragment of the invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In one aspect, the invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore. this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

The proteins may be chemically conjugated, or expressed as recombinant fusion proteins allowing increased levels to be produced in an expression system as compared to non-fused protein. The fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

Fusion partners include protein D from *Haemophilus influenza* B and the non-structural protein from influenzae virus. NS1 (hemagglutinin). Another immunological fusion partner is the protein known as LYTA. Preferably the C terminal portion of the molecule is used. Lyta is derived from *Streptococcus pneumoniae* which synthesize an N-acetyl-L-alanine amidase, amidase LYTA. (coded by the lytA gene {Gene. 43 (1986) pace 265–272} an autolysin that specifically degrades certain bonds in the peptidoglycan backbone. The C-terminal domain of the LYTA protein is responsible for the affinity to the choline or to some choline analogues such as DEAE. This property has been exploited for the development of *E.coli* C-LYTA expressing plasmids useful for expression of fusion proteins. Purification of hybrid proteins containing the C-LYTA fragment at its amino terminus has been described {Biotechnology: 10. (1992) page 795–798}. It is possible to use the repeat portion of the Lyta molecule found in the C terminal end starting at residue 178, for example residues 188–305.

The present invention also includes variants of the aforementioned polypeptides, that is polypeptides that vary from the referents by conservative amino acid substitutions, whereby a residue is substituted by another with like characteristics. Typical such substitutions are among Ala Val. Leu and Ile; among Ser and Thr; among the acidic residues Asp and Glu; among Asn and Gln; and among the basic residues Lys and Arg; or aromatic residues Phe and Tyr. Particularly preferred are variants in which several. 5–10, 1–5, 1–3, 1–2 or 1 amino acids are substituted deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect the present invention relates to CASB414 polynucleotides. Such polynucleotides include isolated polynucleotides comprising a nucleotide sequence encoding a polypeptide which has at least 70% identity, preferably at least 80% identity, more preferably at least 90% identity, yet more preferably at least 95% identity, to the amino acid sequence of SEQ ID NO:2, over the entire length of SEQ ID NO:2. In this regard. polypeptides which have at least 97% identity are highly preferred, whilst those with at least 98–99% identity are more highly preferred, and those with at least 99% identity are most highly preferred. Such polynucleotides include a polynucleotide comprising the nucleotide sequence contained in SEQ ID NO:1 encoding the polypeptide of SEQ ID NO:2.

Further polynucleotides of the present invention include isolated polynucleotides comprising a nucleotide sequence that has at least 70% identity, preferably at least 80% identity, more preferably at least 90% identity, yet more preferably at least 95% identity, to a nucleotide sequence encoding a polypeptide of SEQ ID NO:2, over the entire coding region. In this regard, polynucleotides which have at least 97% identity are highly preferred, whilst those with at least 98–99% identity are more highly preferred, and those with at least 99% identity are most highly preferred.

Further polynucleotides of the present invention include isolated polynucleotides comprising a nucleotide sequence which has at least 70% identity, preferably at least 80% identity, more preferably at least 90% identity, yet more preferably at least 95% identity, to SEQ ID NO:1 over the entire length of SEQ ID NO:1. In this regard, polynucleotides which have at least 97% identity are highly preferred, whilst those with at least 98–99% identity are more highly preferred, and those with at least 99% identity are most highly preferred. Such polynucleotides include a polynucleotide comprising the polynucicotide of SEQ ID NO:1 as well as the polynucleotide of SEQ ID NO.1. Said polynucleotide can be inserted in a suitable plasmid or recombinant microorganism vector and used for immunization ( see for example Wolff et. al., Science 247:1465–1468 (1990); Corr et. al., J. Exp. Med. 184:1555–1560 (1996); Doe et al., Proc. Natl. Acad. Sci. 93:8578–8583 (1996)) The invention also provides polynucleotides which are complementary to all the above described polynucleotides.

The invention also provides a fragment of a CASB414 polynucleotide which when administered to a subject has the same immunogenic properties as the polynucleotide of SEQ ID NO:1.

The invention also provides a polynucleotide encoding an immunological fragment of a CASB414 polypeptide as hereinbefore defined.

The nucleotide sequence of SEQ ID NO:1 shows homology with mouse intelectin (GenBank accession AB016496). The nucleotide sequence of SEQ ID NO:1 is a cDNA sequence and comprises a polypeptide encoding sequence (nucleotide 102 to 1043) encoding a polypeptide of 313 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of the SEQ ID NO:2 is structurally related to other proteins of the lectin family. having homology and/or structural similarity with mouse intelectin (accession 3357909).

Preferred polypeptides and polynucleotides of the present invention are expected to have, inter alia, similar biological functions/properties to their homologous polypeptides and polynucleotides. Furthermore, preferred polypeptides, immunological fragments and polynucleotides of the present invention have at least one activity of either SEQ ID NO:1 or SEQ ID NO:2, as appropriate.

The present invention also relates to partial polynucleotide and polypeptide sequences which were first identified prior to the determination of the corresponding full length sequences of SEQ ID NO:1 and SEQ ID NO:2.

Accordingly, in a further aspect, the present invention provides for an isolated polynucleotide which:

(a) comprises a nucleotide sequence which has at least 70% identity, preferably at least 80% identity, more preferably at least 90% identity, yet more preferably at least 95% identity, even more preferably at least 97–99% identity to SEQ ID NO:3 over the entire length of SEQ ID NO:3;

(b) has a nucleotide sequence which has at least 70% identity, preferably at least 80% identity, more preferably at least 90% identity, yet more preferably at least 95% identity, even more preferably at least 97–99% identity, to SEQ ID NO:1 over the entire length of SEQ ID NO:3;

(c) the polynucleotide of SEQ ID NO:3; or (d) a nucleotide sequence encoding a polypeptide which has at least 70% identity, preferably at least 80% identity, more preferably at least 90% identity, yet more preferably at least 90% identity, even more preferably at least 97–99% identity, to the amino acid sequence of SEQ ID NO:4, over the entire length of SEQ ID NO:4; as well as the polynucleotide of SEQ ID NO:3.

The present invention further provides for a polypeptide which:

(a) comprises an amino acid sequence which has at least 70% identity, preferably at least 80% identity, more preferably at least 90% identity, yet more preferably at least 95% identity, most preferably at least 97–99% identity, to that of SEQ ID NO:2 over the entire length of SEQ ID NO:4;

(b) has an amino acid sequence which is at least 70% identity, preferably at least 80% identity, more preferably at least 90% identity, yet more preferably at least 95% identity. most preferably at least 97–99% identity, to the amino acid sequence of SEQ ID NO:2 over the entire length of SEQ ID NO:4;

(c) comprises the amino acid of SEQ ID NO:4; and (d) is the polypeptide of SEQ ID NO:4;

as well as polypeptides encoded by a polynucleotide comprising the sequence contained in SEQ ID NO:3.

The nucleotide sequence of SEQ ID NO:3 and the peptide sequence encoded thereby are derived from EST (Expressed Sequence Tag) sequences. It is recognised by those skilled in the art that there will inevitably be some nucleotide sequence reading errors in EST sequences (see Adams. M. D. et al. Nature 377 (supp) 3, 1995). Accordingly, the nucleotide sequence of SEQ ID NO:3 and the peptide sequence encoded therefrom are therefore subject to the same inherent limitations in sequence accuracy. Furthermore, the peptide sequence encoded by SEQ ID NO:3 comprises a region of identity or close homology and/or close structural similarity (for example a conservative amino acid difference) with the closest homologous or structurally similar protein.

Polynucleotides of the present invention may be obtained, using standard cloning and screening techniques, from a cDNA library derived from mRNA in cells of human colon cancer, (for example Sambrook et al., Molecular Cloning: A Laboratory Manual, $2^{nd}$ Ed., Cold Spring harbor Laboratory Press. Cold Spring harbor. N.Y. (1989). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself: or the coding sequence for the mature polypeptide in reading frame with other coding sequences, such as those encoding a leader or secretory sequence, a pre- or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen. Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in SEQ ID NO:1, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides. Particularly preferred primers will have between 20 and 25 nucleotides. In particular, polypeptides or polynucleotides derived from sequences from homologous animal origin could be used as immunogens to obtain a cross-reactive immune response to the human gene.

A polynucleotide encoding a polypeptide of the present invention, including homologous from species other than human, may be obtained by a process which comprises the steps of screening an appropriate library under stringent hybridization conditions with a labeled probe having the sequence of SEQ ID NO:1 or a fragment thereof: and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl. 15 mM trisodium citrate). 50 mM sodium phosphate (pH7.6). 5×Dennardt's solution. 10% dextran sulfate, and 20 microgram/ml denatured, sheared salmon sperm DNA; followed by washing the filters in 0.1 x SSC at about 65° C. Thus the present invention also includes polynucleotides obtainable by screening an appropriate library under stingent hybridization conditions with a labeled probe having the sequence of SEQ ID NO:1 or a fragment thereof.

The skilled artisan will appreciate that, in many cases, an isolated cDNA sequence will be incomplete, in that the region coding for the polypeptide is short at the 5' end of the cDNA.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85. 8998–9002. 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is. primers designed 10 anneal within the amplified product (typically an adaptor specific primer that anneals further 3' in the adaptor sequence and a gene specific primer that anneals further 5' in the known gene sequence). The products of this reaction can then be analysed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression Systems. Accordingly, in a further aspect the present invention relates to an expression system which comprises a polynucleotide of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production host cells can be genetically engineered to incorporate expression systems or portions thereof for polynucleotides of the present invention. Introduction of polynucleotides into host cells can be effected by methods described in many standard laboratory manuals, such as Davis et al. Basic Methods in Molecular Biology (1986) and Sambrook et al., Molecular Cloning: A Laboratory Manual 2nd Ed., Cold Spring Harbor Laboratory Press. Cold Spring Harbor. N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Preferably the proteins of the invention are coexpressed with thioredoxin in trans (TIT). Coexpression of thioredoxin in trans versus in cis is preferred to keep antigen free of thioredoxin without the need for protease. Thioredoxin coexpression eases the solubilisation of the proteins of the invention. Thioredoxin coexpression has also a significant impact on protein purification yield, on purified-protein solubility and quality.

Representative examples of appropriate hosts include bacterial cells, such as Streptococci. Staphylococci. *E coli*. Streptomyces and *Bacillus subtilis* cells: fungal cells, such as yeast cells and Aspergillus cells: insect cells such as Drosophila S2 and Spodoptera Sf9 cells; animal cells such as CHO, COS, HeLa C127.3T3, BHK, HEK 293 and Bowes melanoma cells: and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., Molecular Cloning, A Laboratory Manual (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses. Viruses and bacteria used for this purpose are for instance: poxviruses (e.g: vaccinia fowlpox, canarypox). alphaviruses (Sindbis virus. Semliki Forest Virus. Venezuelian Equine Encephalitis Virus), adenoviruses, adeno-associated virus, picornaviruses (poliovirus, rhinovirus), herpesviruse (varicella zoster virus, etc). Listeria Salmonella. Shigella, BCG. These viruses and bacteria can be virulent, or attenuated in various ways in order to obtain live vaccines. Such live vaccines also form part of the invention.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

Another important aspect of the invention relates to a method for inducing, re-inforcing or modulating an immunological response in a mammal which comprises inoculating the mammal with a fragment or the entire polypeptide or polynucleotide of the invention, adequate to produce antibody and/or T cell immune response for prophylaxis or for therapeutic treatment of cancer and autoinmmune disease and related conditions. Yet another aspect of the invention relates to a method of inducing, re-inforcing or modulating immunological response in a mammal which comprises, delivering a polypeptide of the present invention via a vector or cell directing expression of the polynucleotide and coding for the polypeptide in vivo in order to induce such an immunological response to produce immune responses for prophylaxis or treatment of said mammal from diseases.

A further aspect of the invention relates to an immunological/vaccine formulation (composition) which, when introduced into a mammalian host, induces, re-inforces or modulates an immunological response in that mammal to a polypeptide of the present invention wherein the composition comprises a polypeptide or polynucleotide of the invention or an immunological fragment thereof as herein before defined. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain antioxidants, buffers, bacteriostats and solutes which render the formulation isotonic with the blood of the recipient, and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

A further aspect of the invention relates to the in vitro induction of immune responses to a fragment or the entire polypeptide or polynucleotide of the present invention or a molecule comprising the polypeptide or polynucleotide of the present invention, using cells from the immune system of a mammal, and reinfusing these activated immune cells of the mammal for the treatment of disease. Activation of the cells from the immune system is achieved by in vitro incubation with the entire polypeptide or polynucleotide of the present invention or a molecule comprising the polypeptide or polynucleotide of the present invention in the presence or absence of various immunomodulator molecules. A further aspect of the invention relates to the immunization of a mammal by administration of antigen presenting cells modified by in vitro loading with part or the entire polypeptide of the present invention or a molecule comprising the polypeptide of the present invention and administered in vivo in an inmunogenic way. Alternatively, antigen presenting cells can be transfected in vitro with a vector containing a fragment or the entire polynucleotide of the present invention or a molecule comprising the polynucleotide of the present invention, such as to express the corresponding polypeptide, and administered in vivo in an immunogenic way.

The vaccine formulation of the invention may also include adjuvant systems for enhancing the immunogenicity of the formulation. Preferably the adjuvant system raises preferentially a TH1 type of response.

An immune response may be broadly distinguished into two extreme catagories, being a humoral or cell mediated immune responses (traditionally characterised by antibody and cellular effector mechanisms of protection respectively). These categories of response have been termed TH1-type responses (cell-mediated response), and TH2-type immune responses (humoral response). Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1. IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4 +ve T cell clones by Mosmann and Coffman (Mosmann, T. R. and Coffman, R. L. (1989) TH1 and TH2 cells: different patterns of lymphokine secretion lead to different functional properties. *Annual Review of Immunology*, 7, p145–173). Traditionally, TH1-type responses are associated with the production of the INF-γ and IL-2 cytokines by T-lymphocytes. Other cytokines often directly associated with the induction of TH1-type immune responses are not produced by T-cells, such as IL-12. In contrast. TH2-type responses are associated with the secretion of IL-4, IL-5, IL-6 and IL-13.

It is known that certain vaccine adjuvants are particularly suited to the stimulation of either TH1 or TH2-type cytokines responses. Traditionally the best indicators of the TH1:TH2 balance of the immune response after a vaccination or infection includes direct measurement of the production of TH1 or TH2 cytokines by T lymphocytes in vitro after restimulation with antigen, and/or the measurement of the IgG1:IgG2a ratio of antigen specific antibody responses.

Thus, a TH1-type adjuvant is one which preferentially stimulates isolated T-cell populations to produce high levels of TH1-type cytokines when re-stimulated with antigen in vitro, and promotes development of both CD8+cytotoxic T lymphocytes and antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4. 5 or 6 acylated chains and is manufactured by Ribi Immunochem. Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22micron membrane (European Patent number 0 689 454). 3D-MPL will be present in the range of 10 $\mu$g–100 $\mu$g preferably 25–50 $\mu$g per dose wherein the antigen will typically be present in a range 2–50 $\mu$g per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with an carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21:3D-MPL will typically be in the order of 1:10 to 10:1; preferably 1:5 to 5:1 and often substantially 1:1. The preferred range for optimal synergy is 2.5:1 to 1:1 3D-MPL: QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 $\mu$g–200 $\mu$g, such as 10–100 $\mu$g, preferably 10 $\mu$g–50 $\mu$g per dose. Typically the oil in water will comprise from 2 to 10% squalene, from 2 to 10% alpha tocopherol and from 0.3 to 3% tween 80. Preferably the ratio of squalene: alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g.

Tween 80, in an aqueous carrier. The aqueous carrier may be, for example, phosphate buffered saline.

A particularly potent adjuvant formulation involving QS21.3D-MPL and tocopherol in an oil in water emulsion is described in WO 95/17210.

The present invention also provides a polyvalent vaccine composition comprising a vaccine formulation of the invention in combination with other antigens, in particular antigens useful for treating cancers, autoimmune diseases and related conditions. Such a polyvalent vaccine composition may include a TH-1 inducing adjuvant as hereinbefore described.

This invention also relates to the use of polynucleotides of the present invention as diagnostic reagents. Detection of a mutated form of the gene characterised by the polynucleotide of SEQ ID NO:1 which is associated with a dysfunction will provide a diagnostic tool that can add to, or define, a diagnosis of a disease, or susceptibility to a disease, which results from under-expression, over-expression or altered spatial or temporal expression of the said gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype, Point mutations can be identified by hybridizing amplified DNA to labeled CASB414 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (ee, e.g., Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401). In another embodiment, an array of oligonucleotides probes comprising CASB414 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M.Chee et al., Science, Vol 274, pp 610–613 (1996)).

The diagnostic assays offer a process for diagnosing or determining a susceptibility to cancers, autoimmune disease and related conditions through detection of mutation in the CASB414 nucleotide sequence by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides. Assay techniques that can be used to determine levels of a protein, such as a polypeptide of the present invention, in a sample derived from a host are well-known to those of skill in the art.

Thus in another aspect, the present invention relates to a diagnostic kit for performing a diagnostic assay which comprises:
(a) a polynucleotide of the present invention, preferably the nucleotide sequence of SEQ ID NO:1, or a fragment thereof;
(b) a nucleotide sequence complementary to that of (a);
(c) a polypeptide of the present invention, preferably the polypeptide of SEQ ID NO:2 or a fragment thereof; or
(d) an antibody to a polypeptide of the present invention, preferably to the polypeptide of SEQ ID NO:2.

The nucleotide sequences of the present invention are also valuable for chromosomal localisation. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick. Mendelian Inheritance in Man (available on-line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

In a further aspect the invention provides an antibody immunospecific for a polypeptide according to the invention or an immunological fragment thereof as hereinbefore defined. Preferably the antibody is a monoclonal antibody.

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor er al., Immunology Today (1983) 4:72) and the EBV-hybridoma technique (Cole et al., Monoclonal Antibodies and Cancer Therapy, 77–96. Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography. The antibody of the invention may also be employed to prevent or treat cancer, particularly colon cancer, autoimmune disease and related conditions.

Another aspect of the invention relates to a method for inducing or modulating an immunological response in a mammal which comprises inoculating the mammal with a polypeptide of the present invention, adequate to produce antibody and/or T cell immune response to protect or ameliorate the symptoms or progression of the disease. Yet another aspect of the invention relates to a method of inducing or modulating immunological response in a mammal which comprises, delivering a polypeptide of the present invention via a vector directing expression of the polynucleotide and coding for the polypeptide in vivo in order to induce such an immunological response to produce antibody to protect said animal from diseases.

It will be appreciated that the present invention therefore provides a method of treating abnormal conditions such as, for instance, cancer and autoimmune diseases, in particular, colon cancer, related to either a presence of, an excess of, or an under-expression of, CASB414 polypeptide activity.

The present invention further provides for a method of screening compounds to identify those which stimulate or which inhibit the function of the CASB414 polypeptide. In general, agonists or antagonists may be employed for therapeutic and prophylactic purposes for such diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof (see Coligan et al., Current Protocols in Immunology 1(2):Chapter 5 (1991)). Screening methods will be known to those skilled in the art. Further screening methods may be found in for example D. Bennett et al., J Mol Recognition. 8:52–58 (1995); and K. Johanson et al., J Biol Chem, 270(16):9459–9471 (1995) and references therein.

Thus the invention provides a method for screening to identify compounds which stimulate or which inhibit the function of the polypeptide of the invention which comprises a method selected from the group consisting of:

(a) measuring the binding of a candidate compound to the polypeptide (or to the cells or membranes bearing the polypeptide) or a fusion protein thereof by means of a label directly or indirectly associated with the candidate compound;

(b) measuring the binding of a candidate compound to the polypeptide (or to the cells or membranes bearing the polypeptide) or a fusion protein thereof in the presense of a labeled competitior;

(c) testing whether the candidate compound results in a signal generated by activation or inhibition of the polypeptide, using detection systems appropriate to the cells or cell membranes bearing the polypeptide;

(d) mixing a candidate compound with a solution containing a polypeptide of claim 1, to form a mixture, measuring activity of the polypeptide in the mixture, and comparing the activity of the mixture to a standard; or (e) detecting the effect of a candidate compound on the production of mRNA encoding said polypeptide and said polypeptide in cells, using for instance, an ELISA assay.

The polypeptide of the invention may be used to identify membrane bound or soluble receptors, if any, through standard receptor binding techniques known in the art. Well known screening methods may also be used to identify agonists and antagonists of the polypeptide of the invention which compete with the binding of the polypeptide of the invention to its receptors, if any.

Thus in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:

(a) a polypeptide of the present invention;

(b) a recombinant cell expressing a polypeptide of the present invention;

(c) a cell membrane expressing a polypeptide of the present invention; or (d) antibody to a polypeptide of the present invention; which polypeptide is preferably that of SEQ ID NO:2.

It will be readily appreciated by the skilled artisan that a polypeptide of the present invention may also be used in a method for the structure-based design of an agonist, antagonist or inhibitor of the polypeptide, by:

(a) determining in the first instance the three-dimensional structure of the polypeptide:

(b) deducing the three-dimensional structure for the likely reactive or binding site(s) of an agonist, antagonist or inhibitor;

(c) synthesing candidate compounds that are predicted to bind to or react with the deduced binding or reactive site; and (d) testing whether the candidate compounds are indeed agonists, antagonists or inhibitors.

Gene therapy may also be employed to effect the endogenous production of CASB414 polypeptide by the relevant cells in the subject. For an overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

Vaccine preparation is generally described in Pharmaceutical Biotechnology, Vol.61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of protein in each vaccine dose is selected as an amount which induces an immunoprotective response without significant, adverse side effects in typical vaccinees. Such amount will vary depending upon which specific immunogen is employed. Generally, it is expected that each dose will comprise 1–1000 µg of protein, preferably 2–100 µg, most preferably 4–40 µg. An optimal amount for a particular vaccine can be ascertained by standard studies involving observation of antibody titres and other responses in subjects. Following an initial vaccination, subjects may receive a boost in about 4 weeks.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide. which may be unmodified RNA or DNA or modified RNA or DNA including single and double stranded regions.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions. additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press. New York, 1988; Biocomputing; Informatics and Genome Projects, Smith, D. W., ed., Academic Press. New York. 1993; Computer Analysis of Sequence Data. Part I. Griffin, A. M., and Griffin, H. G., eds., Humana Press. New Jersey. 1994: Sequence Analysis in Molecular Biology, von Heinje, G., Academic Press. 1987; and Sequence Analysis Primer. Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., *J. Molec. Biol.* 215: 403–410 (1990). The BLAST X program is publicly available from NCBI and other sources (BLAST Manual, Altschul, S., et al., NCBI NLM NIH Bethesda, MD 20894; Altschul. S., et al., J. Mol. Biol. 215: 403–410 (1990). The well known Smith Waterman algorithm may also be used to determine identity.

The preferred algorithm used is FASTA. The preferred parameters for polypeptide or polynuleotide sequence comparison using this algorithm include the following:

Gap Penalty:12

Gap extension penalty:4

Word size: 2, max 6

Preferred parameters for polypeptide sequence comparison with other methods include the following:

1) Algorithm: Needleman and Wunsch, J. Mol Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group. Madison Wis. The aforementioned parameters are the default parameters for polypeptide comparisons (along with no penalty for end gaps).

Preferred parameters for polynucleotide comparison include the following:

1) Algorithm: Needleman and Wunsch, J. Mol Biol. 48: 443–453 (1970)

Comparison matrix: matches=+10, mismatch=0

Gap Penalty:50

Gap Length Penalty:3

A propram useful with these parameters is publicly available as the "gap" program from Genetics Computer Group, Madison Wis. The aforementioned parameters are the default parameters for polynucleotide comparisons.

By way of example, a polynucleotide sequence of the present invention may be identical to the reference sequence of SEQ ID NO:1 that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot Y),$$

wherein $n_n$ is the number of nucleotide alterations, $x_n$ is the total number of nucleotides in SEQ ID NO:1, and y is, for instance. 0.70 for 70%, 0.80 for 80%, 0.85 for 85%. 0.90 for 90%. 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense. missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \leq x_a - (x_a \cdot Y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $X_a$ and y is rounded down to the nearest integer prior to subtracting it from $x_a$.

"Homolog" is a generic term used in the art to indicate a polynucleotide or polypeptide sequence possessing a high degree of sequence relatedness to a subject sequence. Such relatedness may be quntified by determining the degree of identity and/or similarity between the sequences being compared as hereinbefore described. Falling within this generic term are the terms "ortholog", meaning a polynucleotide or polypeptide that is the functional equivalent of a polynucleotide or polypeptide in another species and "paralog" meaning a functionally similar sequence when considered within the same species.

EXAMPLES

Example 1

A Database Screening Method Used to Select Novel Genes that are Differentially Expressed in Cancers 1.1 Introduction A complementary approach to experimental antigen discovery is to explore the human genome databases, particularly those of "Expressed Sequence Tags" (ESTs), in search of tumour-specific and tumour-associated antigens. ESTs are small fragments (approximately 300 bp) of cDNA made from a collection of MRNA extracted from a particular tissue or cell line. Such currently provide a massive amount of ESTs ($10^6$) from several hundreds of cDNA tissue libraries, including tumoural tissues from various types and states of disease. By means of specifically designed informatics tools one can search in this database for a subset of potential antigen candidates, provided that artifacts are carefully avoided. To allow a specific selection, the libraries, from both healthy and diseased tissues, have first to be selected on the basis of different quality criteria (tissue quality, library construction method, sequencing depth and quality, diversity index, frameshift). The EST sequences from these selected libraries are then compared to identify those genes specifically expressed, or significantly overexpressed, in tumoural tissues. Currently, the method is limited by the sequencing depth of these libraries, i.e. typically only about 10% of all the expressed genes of a particular tissue are represented by ESTs from a particular library. This limitation can be overcome by pooling tissue libraries.

After a careful screening using a set of defined criteria (novelty of the gene, putative expression pattern), the selected candidates can be further tested for selective expression in normal and tumoural tissues, for example by RT-PCR.

1.2 Method

The original EST database is reorganized by assembling all the fragments into overlapping "genetic clusters". There are several well known algorithms which can be used to produce these assemblies. Each resulting assembly is thus a consensus sequence representing a fragment of, or a complete gene. This process reduces the total amount of information by one order of magnitude.

The method allows to select candidates by "customized differential expression" by ranking the number of ESTs by customizable tissue category. The data are organized in a relational database comprising Table "ESTs": contains at least the EST names or Ids and the code of the cDNA library from which each EST was generated Table "Assemblies": contains at least for each assembly the list of EST components Table "Libraries": contains at least for each cDNA library its code, tissue or cell line type, disease state (normal, tumour or non-tumoural disease) Links are made between these tables as shown in FIG. 1.

Figure 2:
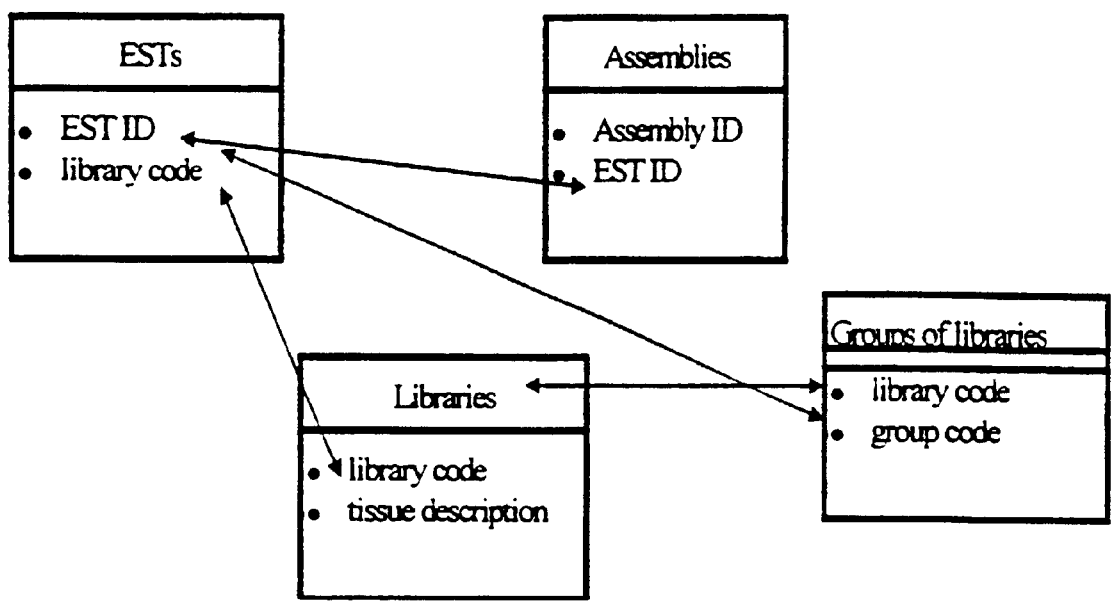

The cDNA libraries are then classified in 5 categories, each subdivided in several groups:

groups of cell lines (separated normal & cancer cell lines)
groups of non-cancerous diseased tissues
group of fetal/embryonic tissues
groups of normal tissues
groups of tumoural tissues
1 group of unknown origin An additional table is then added to the relational database, called "Groups of libraries" as shown in FIG. 2.

The next step is the computing, for each assembly, of the number of ESTs originating from each group of libraries (for example using a Sybase Query Language query):

For each assembly
  For each EST
    Check the corresponding library code
    Assign the corresponding group code
    Count the number of ESTs assigned to the same group code
    Count the total number of ESTs The result of this step is a table called "Results" containing one line per assembly, and one column per group code, and containing the final EST counts.

The table "Results" is used to compute several quantities for each assembly:

"a tumour-to-normal ratio" (TNR):
(sum of EST_T, EST_F, EST_P, EST_O, EST_Tes, EST_Pl) /total number of ESTs where (EST_T) is the sum of all ESTs belonging to the groups that are tissue or cell line tumours. (EST_F) is the sum of all ESTs belonging to groups of fetal tissues or cell lines, EST_P is the total number of ESTs from normal prostate tissue. EST_O is the sum of ESTs from normal ovarian tissues, EST_Tes is the total number of ESTs from normal testis tissues or cell lines, and EST_Pl is the total number of ESTs from placenta tissues. Note that some normal tissues are included, namely "dispensable" tissues like testis, ovary and prostate, which may often share expression patterns with tumours (the so-called "cancer-testis antigens" or CT-antigens), as well as placental, fetal and embryonic tissues.

Any other sum that is relevant to select candidates for a specific target cancer or type of cancers. As an example, one may sum the ESTs from the groups of libraries from tumour tissues or cell lines representative of breast turnouts and from testis and fetal tissues. This may be relevant to detect the above-mentioned CT-antigens.

The resulting table is called "Customized results", and contains one line per assembly and one column per computed sum as well as any other relevant information, such as the total number or ESTs.

The "Customized results" table is then sorted according to the desired use. A relevant sorting is to use the TNR column as a primary sorting key, and the customized sum as the secondary sorting key.

Each assembly over a defined threshold (for example: TNR>0.8) is then compared to a sequence database of known genes or gene products using any sequence comparison algorithm (for example Blast) to screen for novelty of the gene. In a similar way, a sequence comparison can be performed using the original EST or assembly database to check for alternate splicing variants.

1.3 Results

Screening of the previously assembled GenBank EST databases (December 1997) was carried out.

Customized sum: Sum of the ESTs from originating from libraries made from breast cancer, prostate cancer or colon cancer tissues or cell lines (called BPC)

Sorting of the resulting "Customized Results" table (Table 1) is done as follows:
Primary sorting key: descending BPC values
Secondary sorting key: descending TNR values
CASB414 is ranked 9th:

TABLE 1

| Rank | TNR ratio | Total_tumour ESTs | BPC | Fetal | Total number of ESTs | comments |
|---|---|---|---|---|---|---|
| 1 | 0.42635658 | 90 | 90 | 2 | 129 | PSA |
| 2 | 0.66666666 | 69 | 64 | 4 | 96 | novel |
| 3 | 0.84210526 | 35 | 33 | 0 | 38 | intestinal trefoil factor precursor |
| 4 | 0.88235294 | 15 | 13 | 2 | 17 | novel |
| 5 | 0.51724137 | 21 | 13 | 2 | 29 | novel |
| 6 | 0.31372549 | 23 | 11 | 8 | 51 | Her2/neu |
| 7 | 0.36 | 13 | 10 | 2 | 25 | ubiquitin carrier protein |
| 8 | 0.33333333 | 17 | 9 | 2 | 33 | eukaryotic initiation factor 2B-epsilon |
| 9 | 0.58333333 | 8 | 8 | 1 | 12 | Novel = CASB414 |

EST distribution shows expression in fetal tissues and colon cancer.

1.4 References

Wan J. S., Sharp S. J., Poirier G. M.-C., Wagaman P. C., Chambers J., Pyati J., Hom Y.-L., Galindo J. E., Huvar A., Peterson P. A., Jackson M. R., Erlander M. G. (1996) Nature Biotechnol. 14, 1685.

Pardoll D. M. (1996) Curr. Opin. Immunom. 8, 619.

Example 2

Qualitative RT-PCR Amplification

Presence of mRNA transcripts in a panel of normal tissues and a small number of tumour samples is evaluated by non-quantitative RT-PCR.

Total RNA from 19 normal tissues and 3 tumour samples was purchased from In Vitrogen. mRNA is purified from total RNA after DNAse treatment using oligo-dT magnetic beads (Dynal). 200 ng of MRNA are reverse transcribed (Expand reverse transcriptase, Boehringer) in a 20 µl reaction and 2 µl of this reaction are amplified by PCR (AmpliTaq Gold. Perkin-Elmer) for 32 cycles (Perkin-Elmer 9600 thermocycler) using standard protocols. Non-template controls (NTC) are always included. Amplification products (10 µl) are visualised on ethidium bromide-stained agarose gels. Oligonucleotides for PCR amplification are designed by computer (LaserGene PrimerSelect module). Specificity of the designed oligonucleotides is evaluated in silico by comparing their sequences to the sequences in the public databases using the FASTA algorithm. Transcripts of the housekeeping GAPDH gene are amplified under identical conditions on all tissue samples. GAPDH serves as a positive control and provides a visual reference of a highly expressed gene. Detection of CASB414 mRNA in 19 normal issues and 3 tumour samples by RT-PCR is shown in FIG. 3.

Example 3

Real-time RT-PCR Analysis

Real-time RT-PCR (U. Gibson. 1996. Genome Research: 6,996) is used to compare mRNA transcript abundance of the candidate antigen in tumour and normal colon tissues from multiple patients. In addition, MRNA levels of the candidate gene are re-evaluated by this approach in a panel of normal tissues. Total RNA is extracted from snap frozen colon tissue biopsies using TriPure reagent (Boehringer). Total RNA from normal tissues is from In Vitrogen as above. Poly-$A^+$ mRNA is purified from total RNA after DNAase treatment using oligo-dT magnetic beads (Dynal). Quantification of the mRNA is performed by spectrofluorimetry (BioRad) using SybrII dye (Molecular Probes). Primers for amplification are designed with the Perkin-Elmer Primer Express software using default options for TaqMan amplification conditions.

Real-time reactions are assembled according to standard PCR protocols using 2 ng of purified MRNA for each reaction. SybrI dye (Molecular Probes) is added at a final dilution of 1/5000 for real-time detection. Amplification (40 cycles) and real-time detection is performed in a PE 7700 system. Ct values are calculated using the 7700 Sequence Detector software for the tumour (CtT) and normal (CtN) samples of each patient. The difference between Ct values (CtN−CtT) is a direct measure of the difference in transcript levels between the tumour and normal tissues. As Ct values are log-linearly related to copy number and that the efficiency of PCR amplification under the prevailing experimental conditions is close to the theoretical amplification efficiency. $2^{(CtN-CtT)}$ is an estimate of the relative transcript levels in the two tissues (i.e. fold mRNA over-expression in tumor). The percentage of over-expressing patients and the average level of mRNA over-expression in the tumours of these patients is calculated from the data set of 18 patients. In addition, Ct values obtained with 12 normal tissues are provided for the candidate antigen and beta-actin.

TABLE 2

| Patients over-expressing CASB414 in colon tumours (%) | Average level of over-expression in colon tumours (fold) |
|---|---|
| 16 | 4.4 |

TABLE 3

Real-time RT-PCR Ct values for CASB414 and actin in 12 normal tissues.

|          | Bla | Brai | Bre | Cer | Hea | Kid | Liv | Lun | Oes | Pla | Rec | Ute |
|----------|-----|------|-----|-----|-----|-----|-----|-----|-----|-----|-----|-----|
| CASBC414 | 32  | 40   | 31  | 35  | 26  | 25  | 25  | 25  | 26  | 27  | 20  | 28  |
| Actin    | 14  | 16   | 15  | 15  | 17  | 16  | 17  | 16  | 14  | 15  | 16  | 15  |

Legend. Bla: bladder, Brai: brain, Bre: breast, Cer: cervix, Hea: heart, Kid: kidney, Liv: liver, Lun: lung, Oes: oesophagus, Pla: placenta, Rec: rectum, Ute: uterus.

Example 4

Southern Blot Analysis

Southern blot analysis was performed on 2.5 µg endonuclease digested cDNA plasmid library (see below) using standard protocols. Probes are gel-purified PCR fragments that have been verified by DNA sequencing and labelled with the AlkPhos Direct system (Amersham Pharmacia). Southern blot analysis of CASB414 on restricted cDNA library is shown in FIG. 4.

Example 5

Identification of the Full Length cDNA Sequence

Colon tumour cDNA libraries are constructed using the Lambda Zap II system (Stratagene) from 5 µg of polyA$^+$ MRNA. The supplied protocol is followed except that SuperscriptII (Life Technologies) is used for the reverse transcription step. Oligo dT-primed and random-primed libraries are constructed. About $1.5 \times 10^6$ independent phage are plated for each screening of the library. Phage plaques are transferred onto nylon filters and hybridised using a cDNA probe labelled with AlkPhos Direct. Positive phage are detected by chemiluminescence. Positive phage are excised from the agar plat, eluted in 500 µl SM buffer and confirmed by gene-specific PCR. Eluted phage are converted to single strand M13 bacteriophage by in vivo excision. The bacteriophage is then converted to double strand plasmid DNA by infection of *E. coli*. Infected bacteria are plated and submitted to a second round of screening with the cDNA probe. Plasmid DNA is purified from positive bacterial clones and sequenced on both strands.

When the full length gene cannot be obtained directly from the cDNA library, missing sequence is isolated using RACE technology (Marathon Kit, ClonTech.). This approach relies on reverse transcribing mRNA into double strand cDNA, ligating linkers onto the ends of the cDNA and amplifying the desired extremity of the cDNA using a gene-specific primer and one of the linker oligonucleotides. Marathon PCR products are cloned into a plasmid (pCRII-TOPO, In Vitrogen) and sequenced.

Example 6

6.1 Expression and Purification of Tumour-specific Antigens

Expression in microbial hosts is used to produce the antigen of the invention for vaccine purposes and to produce protein fragments or whole protein for rapid purification and generation of antibodies needed for characterization of the naturally expressed protein by immunohistochemistry or for follow-up of purification.

Recombinant proteins may be expressed in two microbial hosts, *E. coli* and in yeast (such as Saccharomyces cerevisiae or Pichia pastoris). This allows the selection of the expression system with the best features for this particular antigen production. In general, the recombinant antigen will be expressed in *E. coli* and the reagent protein expressed in yeast.

The expression strategy first involves the design of the primary structure of the recombinant antigen. In general an expression fusion partner (EFP) is placed at the N terminal extremity to improve levels of expression that could also include a region useful for modulating the immunogenic properties of the antigen, an immune fusion partner (IFP). In addition, an affinity fusion partner (AFP) useful for facilitating further purification is included at the C-terminal end.

When the recombinant strains are available, the recombinant product is characterized by the evaluation of the level of expression and the prediction of further solubility of the protein by analysis of the behavior in the crude extract.

After growth on appropriate culture medium and induction of the recombinant protein expression, total extracts are analyzed by SDS-PAGE. The recombinant proteins are visualized in stained gels and identified by Western blot analysis using specific antibodies.

A comparative evaluation of the different versions of the expressed antigen will allow the selection of the most promising candidate that is to be used for further purification and immunological evaluation.

The purification work follows a classical approach based on the presence of an His affinity tail in the recombinant protein. In a typical experiment the disrupted cells are filtered and the acellular extracts loaded onto an Ion Metal Affinity Chromatography (IMAC: Ni$^{++}$NTA from Qiagen) that will specifically retain the recombinant protein. The retained proteins are eluted by 0–500 mM Imidazole gradient (possibly in presence of a detergent) in a phosphate buffer. This step is optimally followed by an Anion Exchange resin step and a Size Exclusion chromatography step depending on the success of the Imac step and the nature of the contaminants.

6.2 Antibody Production and Immunohistochemistry

Small amounts of relatively purified protein can be used to generate immunological tools in order to
a) detect the expression by immunohistochemistry in normal or cancer tissue sections;
b) detect the expression, and to follow the protein during the purification process (ELISA/ Western Blot); or
c) characterise/quantify the purified protein (ELISA).

6.2.1 Polyclonal Antibodies:
Immunization

2–3 Rabbits are immunized, intramuscularly (I.M.), 3 times at 3 weeks intervals with 100 µg of protein, formulated in the adjuvant 3D-MPL/QS21 . 3 weeks after each immunisation a blood sample is taken and the antibody titer estimated in the serum by ELISA using the protein as coating antigen following a standard protocol.

ELISA 96 well microplates (maxisorb Nunc) are coated with 5μg of protein overnight at 4° C. After 1 hour saturation at 37° C. with PBS NCS 1%, serial dilution of the rabbit sera is added for 1H 30 at 37° C. (starting at 1/10). After 3 washings in PBS Tween, anti rabbit biotinylated anti serum (Amersham) is added (1/5000). Plates are washed and peroxydase coupled streptavidin (1/5000) is added for 30 min at 37° C. After washing, 50 μl TMB (BioRad) is added for 7 min and the reaction then stopped with $H_2SO_4$ 0.2M. The OD can be measured at 450 nm and midpoint dilutions calculated by SoftmaxPro.

6.2.2 Monoclonal Antibodies:

Immunization

5 BALB/c mice are immunized 3 times at 3 week intervals with 5 μg of purified protein. Bleedings are performed 14 days post II and 1 week post 3. The sera is tested by Elisa on purified protein used as coated antigen. Based on these results (midpoint dilution>10000) one mouse is selected for fusion Fusion/HAT selection Spleen cells are fused with the SP2/0 myeloma according to a standard protocol using PEG 40% and DMSO 5%. Cells are then seeded in 96 well plates $2.5'10^4$–$10^5$ cells/well and resistant clones will be selected in HAT medium. The supernatant of these hybridomas will be tested for their content in specific antibodies and when positive, will be submitted to 2 cycles of limited dilution. After 2 rounds of screening, 3 hybridomas will be chosen for ascitis production.

6.2.3 Immunohistochemistry

When antibodies are available immuno staining is performed on normal or cancer tissue sections, in order to determine:

the level of expression of the protein antigen of the invention in cancer relative to normal tissue or the proportion of cancers of a certain type expressing the antigen if other cancer types also express the antigen the proportion of cells expressing the antigen in a cancer tissue the cellular localisation of the antigen Tissue Sample Preparation After dissection, the tissue sample is mounted on a cork disk in OCT compound and rapidly frozen in isopentane previously super cooled in liquid nitrogen (−160° C.). The block will then be conserved at −70° C. until use. 7–10 μm sections will be realized in a cryostat chamber (−20, −30° C.).

Staining

Tissue sections are dried for 5 min at room Temperature (RT), fixed in acetone for 10 min at RT, dried again, and saturated with PBS 0.5% BSA 5% serum. After 30 min at RT either a direct or indirect staining is performed using antigen specific antibodies. A direct staining leads to a better specificity but a less intense staining whilst an indirect staining leads to a more intense but less specific staining.

6.3 Analysis of human cellular immune responses to the antigen of the invention

The immunological relevance of the antigen of the invention can be assessed by in vitro priming of human T cells. All T cell lymphocyte lines and dendritic cells are derived from PBMCs (peripheral blood mononuclear cells) of healthy donors (preferred HLA-A2 subtype). An HLA-A2.1/$K^b$ transgenic mice is also used for screening of HLA-A2.1 peptides.

Newly discovered antigen-specific CD8+T cell lines are raised and maintained by weekly in vitro stimulation. The lytic activity and the γ-IFN production of the CD8 lines in response to the antigen or antigen derived-peptides is tested using standard procedures.

Two strategies to raise the CD8+T cell lines are used: a peptide-based approach and a whole gene-based approach. Both approaches require the full-length cDNA of the newly discovered antigen in the correct reading frame to be either cloned in an appropriate delivery system or to be used to predict the sequence of HLA binding peptides.

Peptide-based approach The HLA-A2 binding peptide sequences are predicted by the Parker's algorithm. Peptides are then screened in the HLA-A2.1/$K^b$ transgenic mice model (Vitiello et al.). Briefly, transgenic mice are immunized with adjuvanted HLA-A2 peptides, those unable to induce a CD8 response (as defined by an efficient lysis of peptide-pulsed autologous spleen cells) will be further analyzed in the human system. Human dendritic cells (cultured according to Romani et al.) will be pulsed with peptides and used to stimulated CD8-sorted T cells (by Facs). After several weekly stimulations. the CD8 lines will be first tested on peptide-pulsed autologous BLCL (EBV-B transformed cell lines). To verify the proper in vivo processing of the peptide, the CD8 lines will be tested on cDNA-transfected tumour cells (HLA-A2 transfected LnCaP, Skov3 or CAMA tumour cells).

Whole gene-based approach

CD8+ T cell lines will be primed and stimulated with either gene-gun transfected dendritic cells, retrovirally transduced B7.1-transfected fibroblastes, recombinant pox virus (Kim et al.) or adenovirus (Butterfield et al.) infected dentridic cells. Virus infected cells are very efficient to present antigenic peptides since the antigen is expressed at high level but can only be used once to avoid the overgrowth of viral T cells lines.

After alternated stimulations, the CD8 lines are tested on cDNA-transfected tumour cells as indicated above. Peptide specificity and identity is determined to confirm the immunological validation.

References

Vitiello et al. (L. Sherman). J. Exp. Med., J. Exp. Med. 1991, 173:1007–1015.

Romani et al., J. Exp. Med., 1994, 180:83–93.

Kim et al., J. Immunother., 1997. 20:276–286.

Butterfield et al., J. Immunol., 1998, 161:5607–5613.

All publications, including but not limited to patents and patent applications, cited in this specification are herein incorporated by reference as if each individual publication were specifically and individually indicated to be incorporated by reference herein as though fully set forth.

What is claimed is:

1. An isolated polypeptide comprising the amino acid sequence of SEQ ID NO:2.

2. A fusion protein comprising the isolated polypeptide of claim 1.

3. A process of producing an isolated polypeptide comprising (a) culturing a host cell transformed with an expression vector comprising an isolated polynucleotide encoding a polypeptide of claim 1 under conditions sufficient for the production of the encoded polypeptide and (b) recovering the polypeptide.

4. A method for inducing an immune response in a mammal comprising administration of the polypeptide of claim 1 to the mammal, whereby an immune response is induced in the mammal.

* * * * *

SEQUENCE LISTING

<160> NUMBER OF SEQ ID NOS: 4

<210> SEQ ID NO 1
<211> LENGTH: 1215
<212> TYPE: DNA
<213> ORGANISM: homo sapiens

<400> SEQUENCE: 1

```
gaaagctgca ctctgttgag ctccagggcg cagtggaggg agggagtgaa ggagctctct     60
gtacccaagg aaagtgcagc tgagactcag acaagattac aatgaaccaa ctcagcttcc    120
tgctgtttct catagcgacc accagaggat ggagtacaga tgaggctaat acttacttca    180
aggaatggac ctgttcttcg tctccatctc tgcccagaag ctgcaaggaa atcaaagacg    240
aatgtcctag tgcatttgat ggcctgtatt ttctccgcac tgagaatggt gttatctacc    300
agaccttctg tgacatgacc tctggggtg gcggctggac cctggtggcc agcgtgcacg    360
agaatgacat gcgtgggaag tgcacggtgg gcgatcgctg gtccagtcag cagggcagca    420
aagcagtcta cccagagggg gacggcaact gggccaacta caacaccttt ggatctgcag    480
aggcggccac gagcgatgac tacaagaacc ctggctacta cgacatccag gccaaggacc    540
tgggcatctg gcacgtgccc aataagtccc ccatgcagca ctggagaaac agctccctgc    600
tgaggtaccg cacggacact ggcttcctcc agacactggg acataatctg tttggcatct    660
accagaaata tccagtgaaa tatggagaag gaaagtgttg gactgacaac ggcccggtga    720
tccctgtggt ctatgatttt ggcgacgccc agaaaacagc atcttattac tcaccctatg    780
gccagcggga attcactgcg ggatttgttc agttcagggt atttaataac gagagagcag    840
ccaacgcctt gtgtgctgga atgagggtca ccggatgtaa cactgagcac cactgcattg    900
gtggaggagg atactttcca gaggccagtc cccagcagtg tggagatttt tctggttttg    960
attggagtgg atatggaact catgttggtt acagcagcag ccgtgagata actgaggcag   1020
ctgtgcttct attctatcgt tgagagtttt gtgggaggga acccagacct ctcctcccaa   1080
ccatgagatc ccaaggatgg agaacaactt acccagtagc tagaatgtta atggcagaag   1140
agaaaacaat aaatcatatt gactcaaaaa aaaaaaaaa aaaaaaaaaa aaaaaaaaaa   1200
aaaaaaaaaa aaaaa                                                    1215
```

<210> SEQ ID NO 2
<211> LENGTH: 313
<212> TYPE: PRT
<213> ORGANISM: homo sapiens

<400> SEQUENCE: 2

```
Met Asn Gln Leu Ser Phe Leu Leu Phe Leu Ile Ala Thr Thr Arg Gly
 1               5                  10                  15

Trp Ser Thr Asp Glu Ala Asn Thr Tyr Phe Lys Glu Trp Thr Cys Ser
             20                  25                  30

Ser Ser Pro Ser Leu Pro Arg Ser Cys Lys Glu Ile Lys Asp Glu Cys
         35                  40                  45

Pro Ser Ala Phe Asp Gly Leu Tyr Phe Leu Arg Thr Glu Asn Gly Val
     50                  55                  60

Ile Tyr Gln Thr Phe Cys Asp Met Thr Ser Gly Gly Gly Gly Trp Thr
 65                  70                  75                  80

Leu Val Ala Ser Val His Glu Asn Asp Met Arg Gly Lys Cys Thr Val
                 85                  90                  95
```

Gly Asp Arg Trp Ser Ser Gln Gln Gly Ser Lys Ala Val Tyr Pro Glu
            100                 105                 110

Gly Asp Gly Asn Trp Ala Asn Tyr Asn Thr Phe Gly Ser Ala Glu Ala
        115                 120                 125

Ala Thr Ser Asp Asp Tyr Lys Asn Pro Gly Tyr Tyr Asp Ile Gln Ala
    130                 135                 140

Lys Asp Leu Gly Ile Trp His Val Pro Asn Lys Ser Pro Met Gln His
145                 150                 155                 160

Trp Arg Asn Ser Ser Leu Leu Arg Tyr Arg Thr Asp Thr Gly Phe Leu
                165                 170                 175

Gln Thr Leu Gly His Asn Leu Phe Gly Ile Tyr Gln Lys Tyr Pro Val
            180                 185                 190

Lys Tyr Gly Glu Gly Lys Cys Trp Thr Asp Asn Gly Pro Val Ile Pro
        195                 200                 205

Val Val Tyr Asp Phe Gly Asp Ala Gln Lys Thr Ala Ser Tyr Tyr Ser
    210                 215                 220

Pro Tyr Gly Gln Arg Glu Phe Thr Ala Gly Phe Val Gln Phe Arg Val
225                 230                 235                 240

Phe Asn Glu Arg Ala Ala Asn Ala Leu Cys Ala Gly Met Arg Val
                245                 250                 255

Thr Gly Cys Asn Thr Glu His His Cys Ile Gly Gly Gly Tyr Phe
            260                 265                 270

Pro Glu Ala Ser Pro Gln Gln Cys Gly Asp Phe Ser Gly Phe Asp Trp
        275                 280                 285

Ser Gly Tyr Gly Thr His Val Gly Tyr Ser Ser Arg Glu Ile Thr
    290                 295                 300

Glu Ala Ala Val Leu Leu Phe Tyr Arg
305                 310

<210> SEQ ID NO 3
<211> LENGTH: 550
<212> TYPE: DNA
<213> ORGANISM: homo sapiens
<220> FEATURE:
<221> NAME/KEY: misc_feature
<222> LOCATION: (1)...(550)
<223> OTHER INFORMATION: n = A,T,C or G

<400> SEQUENCE: 3
tttcccccag acactggnac ataatctntt gggcatntac ccgaaatttt ccngtgaaat      60
atggagaagg aaagtgttgg actgacaacg gcccggtgat ccctgtggtc tatgattttg     120
cgagcgccca gaaaacagca tcttattact caccctatgg ccagcgggaa ttcactgcgg     180
gatttgttca gttcagggta tttaataacg agagagcagc caacgccttg tgtgctggaa     240
tgagggtcac cggatgtaac actgagcayc actgcattgg tggaggagga tactttccag     300
aggccagtcc ccagcagtgt ggagattttt ctggttttga ttggagtgga tatggaactc     360
atgttggtta cagcagcagc cgtgagataa ctgaggcagc tgtgcttcta ttctatcgtt     420
gagagttttg tgggagggaa cccagacctc tcctcccaac catgagatcc aaggatgga     480 gaacaactta cccagtagct agaatgttaa tggcagaaga gaaaacaata aatcatattg     540
actcaagaaa                                                           550

<210> SEQ ID NO 4
<211> LENGTH: 127
<212> TYPE: PRT

```
<213> ORGANISM: homo sapiens

<400> SEQUENCE: 4

Thr Arg Asn Phe Pro Val Lys Tyr Gly Glu Gly Lys Cys Trp Thr Asp
 1               5                  10                 15

Asn Gly Pro Val Ile Pro Val Val Tyr Asp Phe Ala Ser Ala Gln Lys
            20                  25                 30

Thr Ala Ser Tyr Tyr Ser Pro Tyr Gly Gln Arg Glu Phe Thr Ala Gly
        35                  40                  45

Phe Val Gln Phe Arg Val Phe Asn Asn Glu Arg Ala Ala Asn Ala Leu
    50                  55                  60

Cys Ala Gly Met Arg Val Thr Gly Cys Asn Thr Glu His His Cys Ile
65                  70                  75                  80

Gly Gly Gly Gly Tyr Phe Pro Glu Ala Ser Pro Gln Gln Cys Gly Asp
                85                  90                  95

Phe Ser Gly Phe Asp Trp Ser Gly Tyr Gly Thr His Val Gly Tyr Ser
            100                 105                 110

Ser Ser Arg Glu Ile Thr Glu Ala Ala Val Leu Leu Phe Tyr Arg
            115                 120                 125
```